United States Patent [19]

Wardell

[11] Patent Number: 4,791,354

[45] Date of Patent: Dec. 13, 1988

[54] METHOD FOR MEASURING THE AC ELECTRICAL CONDUCTANCE OF A POLYMERIC COMPOSITE TO DETERMINE HOMOGENEITY OF DISPERSION OF A FILLER

[76] Inventor: Gerald E. Wardell, The Shieling, Killaloe, County Clare, Ireland

[21] Appl. No.: 91,664

[22] Filed: Sep. 1, 1987

Related U.S. Application Data

[63] Continuation of Ser. No. 728,778, Apr. 30, 1985, abandoned.

[30] Foreign Application Priority Data

May 2, 1984 [IE] Ireland .................................. 1094/84

[51] Int. Cl.$^4$ ........................ G01R 27/00; G01R 27/28
[52] U.S. Cl. .............................. 324/65 R; 324/61 R; 324/65 P
[58] Field of Search ................ 324/61 R, 61 P, 65 R, 324/65 P

[56] References Cited

U.S. PATENT DOCUMENTS 4,068,168  1/1978  Boonstra .......................... 324/65 R

FOREIGN PATENT DOCUMENTS 0074780  3/1983  European Pat. Off. .......... 324/61 R Primary Examiner—Reinhard J. Eisenzopf
Assistant Examiner—Jack B. Harvey
Attorney, Agent, or Firm—Curtis, Morris & Safford

[57] ABSTRACT

A method for measuring the AC electrical conductance of a polymeric composite to determine homogeneity of dispersion of a filler is disclosed. The method comprises the steps of applying two spaced apart capacitor plate electrodes closely adjacent to, or onto the surface of the polymeric composite; applying an AC voltage between the electrodes; and measuring the AC current which flows through the polymeric composite from one electrode to the other electrode. The electrodes have a sufficiently large surface area for providing a coupling into the polymeric composite. The coupling shunts the contact resistance of the polymeric composite.

8 Claims, 4 Drawing Sheets

METHOD FOR MEASURING THE AC ELECTRICAL CONDUCTANCE OF A POLYMERIC COMPOSITE TO DETERMINE HOMOGENEITY OF DISPERSION OF A FILLER

This application is a continuation of application Ser. No. 728,778, filed Apr. 30, 1985, now abandoned.

FIELD OF THE INVENTION

This invention relates to a method for the measurement of electrical conductance of a polymeric composite. In particular, it relates to a method for the measurement of electrical conductance of a polymeric composite such as elastomers and plastics which have been made partially conducting by the incorporation of carbon black, metallic powder or other conducting particles.

The measurement of electrical conductance of such a polymeric composite is useful when such composite finds application in an antistatic and conductive product. In addition, conductance measurements provide a useful inferential method for determination of the degree of carbon black dispersion throughout the polymeric composite.

Carbon black is a common reinforcing filler in the production of polymeric composite containing articles such as vehicle tires, hoses, belting, diaphrams, roofing membranes and the like. It can enhance the tear and tensile strength, wear resistance and other physical properties of elastomer products. It is very important that the carbon black particles are adequately dispersed throughout the polymeric matrix as inadequate dispersion can lead to severe problems with post-mixing processes and can also lead to product failure. Overmixing, in an attempt to ensure adequate dispersion, is not good practice as production outputs are lowered and in addition, overmixing causes degradation in the polymer. Mixing equipment is expensive to maintain and can consume over one megawatt of power.

The objective of maintaining correct levels of carbon black dispersion can be difficult to achieve in practice because mixes vary due to changes in raw materials, temperature differences and gradual wear in mixing equipment. Despite the fact that correct dispersion of carbon black is very important, none of the methods currently in use for its determination is wholly satisfactory.

Conventional methods for evaluating carbon black dispersion include optical methods, surface analysis and electrical conductivity.

The Cabot Dispersion Classification is a conventional optical method which views, under a microscope at 77 times magnification, thin microtome sections which are cut with glass knives from a frozen vulcanized composite sample. A standard counting procedure, or comparison with a set of standard photomicrographs, gives a percentage scale of carbon black dispersion. The time required to carry out the method is considerable compared with the rapid progress of batches through successive processing steps. In addition, the sample size is undesirably small having regard to the known prevelance of macroscopic non-homogeneity in factory mixed batches.

Another conventional method is the Stumpe and Railsback optical method which provides a relatively quicker result by visual comparison of a cut surface of composite sample, at 30 times magnification, with a set of standard photomicrographs, rated 1 to 10 from poor to excellent dispersion. This method is quite subjective and different personnel can report quite different ratings with the same specimen. In addition, the method is less reliable if the composite is not vulcanized and the vulcanization step takes typically 20 minutes to carry out.

Still another conventional method is a surface analysis method which employs a stylus type instrument to measure the roughness of a cut surface. A computer records the peaks and valleys as the stylus is drawn across the surface, and calculates a dispersion index based on the roughness values. The surface analysis instrument is delicate and expensive and unvulcanized samples present special problems in cutting.

Electrical conductivity methods are known which enable the determination of carbon black dispersion in both vulcanized and unvulcanized composites. The methods take advantage of the fact that conductivity decreases with improved homogeneity of dispersion due to the progressive separation of conducting carbon particles by insulating polymer. However there are special difficulties associated with the measurement of electrical conductivity in a polymeric composite. For example, three methods are described in BS 2044:1978. One of these methods demands considerable experimental skill while the other two methods require careful and time-consuming sample preparation. The main difficulty lies with the electrode system as certain types of electrodes, when applied to a polymeric composite, have a contact resistance which is many times greater than the inherent resistance of the test specimen and the contact resistance varies considerably having regard to the duration of contact and the pressure of the electrodes on the test specimen.

It will be appreciated that conductance and resistance are related; resistance being the reciprocal of conductance. Therefore measurement of conductance also provides a value of resistance.

An instrument for measuring electrical conductivity of a polymeric composite is described by B. B. Boonstra in Rubber Chemistry and Technology 50, 194–210 (1977). It uses a high force to press a coaxial electrode probe into the polymeric composite thus forming a ring shaped sample in the confined space between the coaxial electrodes. The direct current resistance (or conductance) between the electrodes is measured with an electrometer. It is reported that the measured resistance decreases significantly immediately after pressing the sample but that this change becomes relatively minor after one or two minutes. This instrument reduces the effect of contact resistance by the use of high pressure but there is no assurance that no contact resistance is included in the resistance measured.

It is therefore an object of the present invention to overcome these problems

In particular, it is an object of the present invention to provide a method for measuring the AC electrical conductance of a polymeric composite which avoids the difficulties associated with contact resistance between electrodes and the polymeric composite.

It is still a further object of this invention to provide a method for measuring the electrical conductance of a polymeric composite without physical contact with the material being metered.

It is still a further object of this invention to provide a method for measuring the electrical conductance of a polymeric composite which method is non-destructive.

It is still a further object of this invention to provide a method for measuring the electrical conductance of an unvulcanized polymeric composite.

It is still a further object of this invention to provide a method for measuring the degree of carbon black dispersion in a polymeric composite.

It is still a further object of this invention to provide a method which allows the rapid measurement of carbon black dispersion in a polymeric composite.

SUMMARY OF THE INVENTION

The invention therefore provides a method for measuring the AC electrical conductance of a polymeric composite which method comprises applying two spaced apart capacitor plate electrodes closely adjacent to, or onto the surface of, the polymeric composite, applying an AC voltage between the electrodes and measuring the AC current which flows through the polymeric composite from one electrode to the other electrode, the electrodes having a sufficiently large surface area for providing a coupling into the polymeric composite, which coupling shunts the contact resistance of the polymeric composite.

The method reduces the problem of contact resistance by use of electrodes of sufficiently large area to introduce a significant capacitive coupling between the electrodes and the polymeric composite. In this way a simple and quick measurement of alternating current conductance may be used to test the polymeric composite and the measurement may be related, at least in a qualitative way, to the DC resistance of the polymeric composite, to the resistivity of the polymeric composite or to the homogeneity of dispersion of carbon black in the polymeric composite.

The invention has the additional advantage of being non-destructive with respect to the polymeric composite. The polymeric composite may be vulcanized or unvulcanized.

The method according to the present invention, when applied to measurement of carbon black dispersion in a polymeric composite, offers a high sensitivity at intermediate and good states of dispersion and it has been found that a change of one percent on the Cabot dispersion rating can be equivalent to an order of magnitude change in conductivity. The method also permits the rapid examination of each mix as it is produced and it is believed that no other method can provide such a rapid measurement of electrical conductance and carbon black dispersion in a polymeric composite.

BRIEF DESCRIPTION OF THE DRAWINGS

The invention will be understood in greater detail from the following description of preferred embodiments thereof given by way of example only and with reference to the accompanying drawings in which.

DETAILED DESCRIPTION OF THE PREFERRED EMBODIMENT

Figure 1:
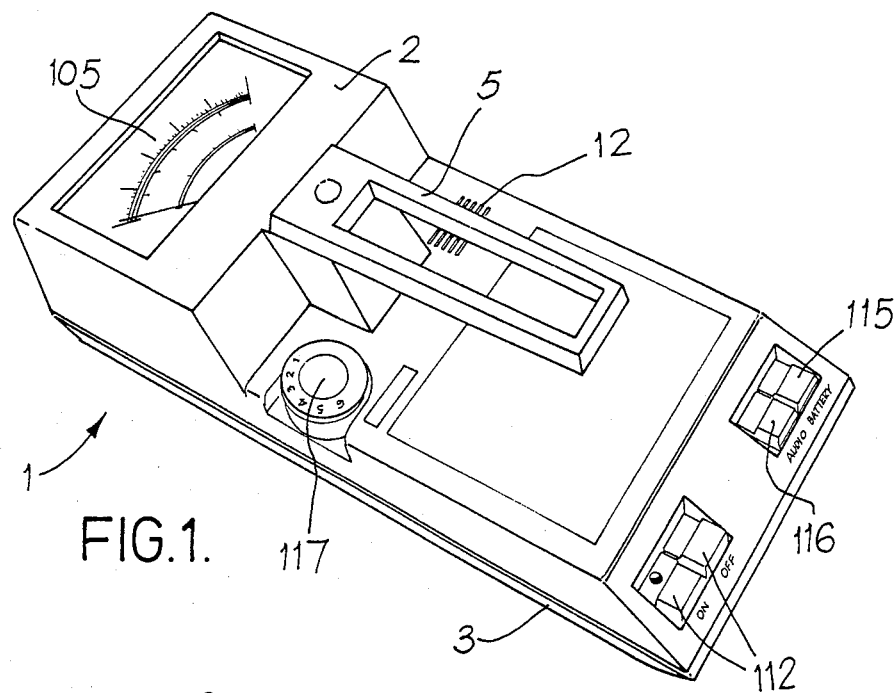
FIG. 1 is a top perspective view of a first embodiment of an apparatus for use in performing the method of the invention.
Figure 2:
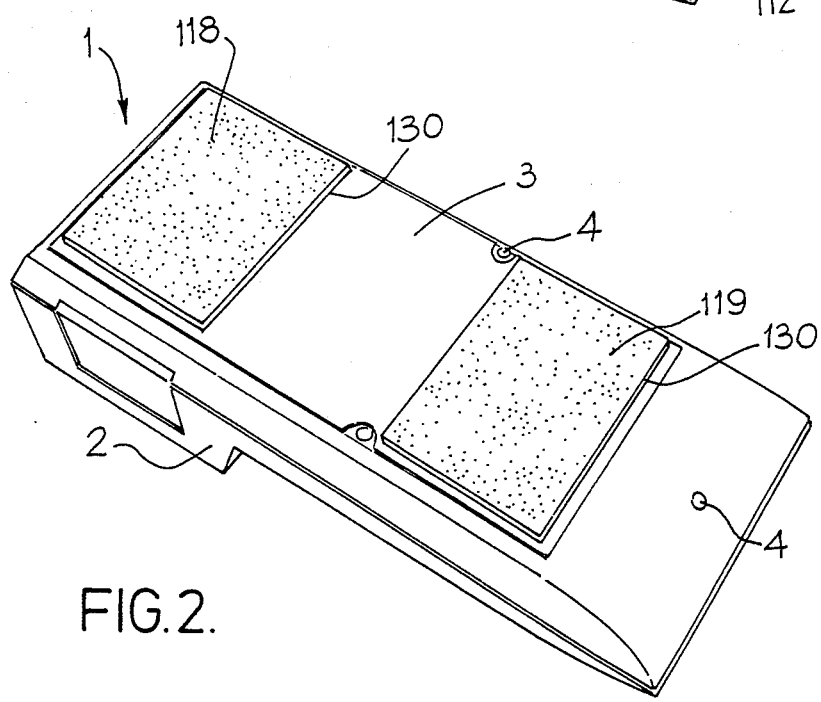
FIG. 2 is an underneath perspective view of the apparatus of FIG. 1.
Figure 3:
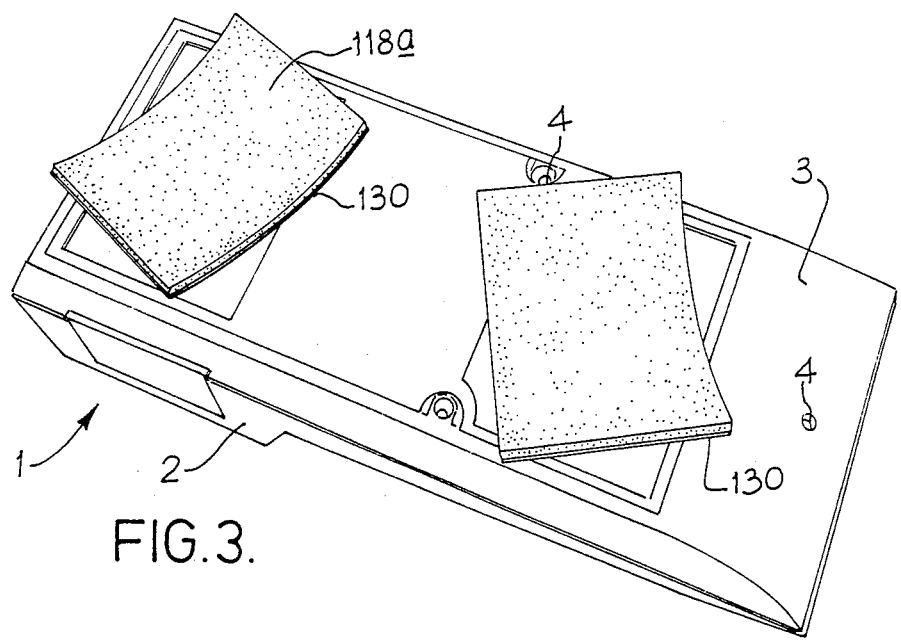
FIG. 3 is an underneath perspective view of a second embodiment of an apparatus according to the invention.
Figure 4:
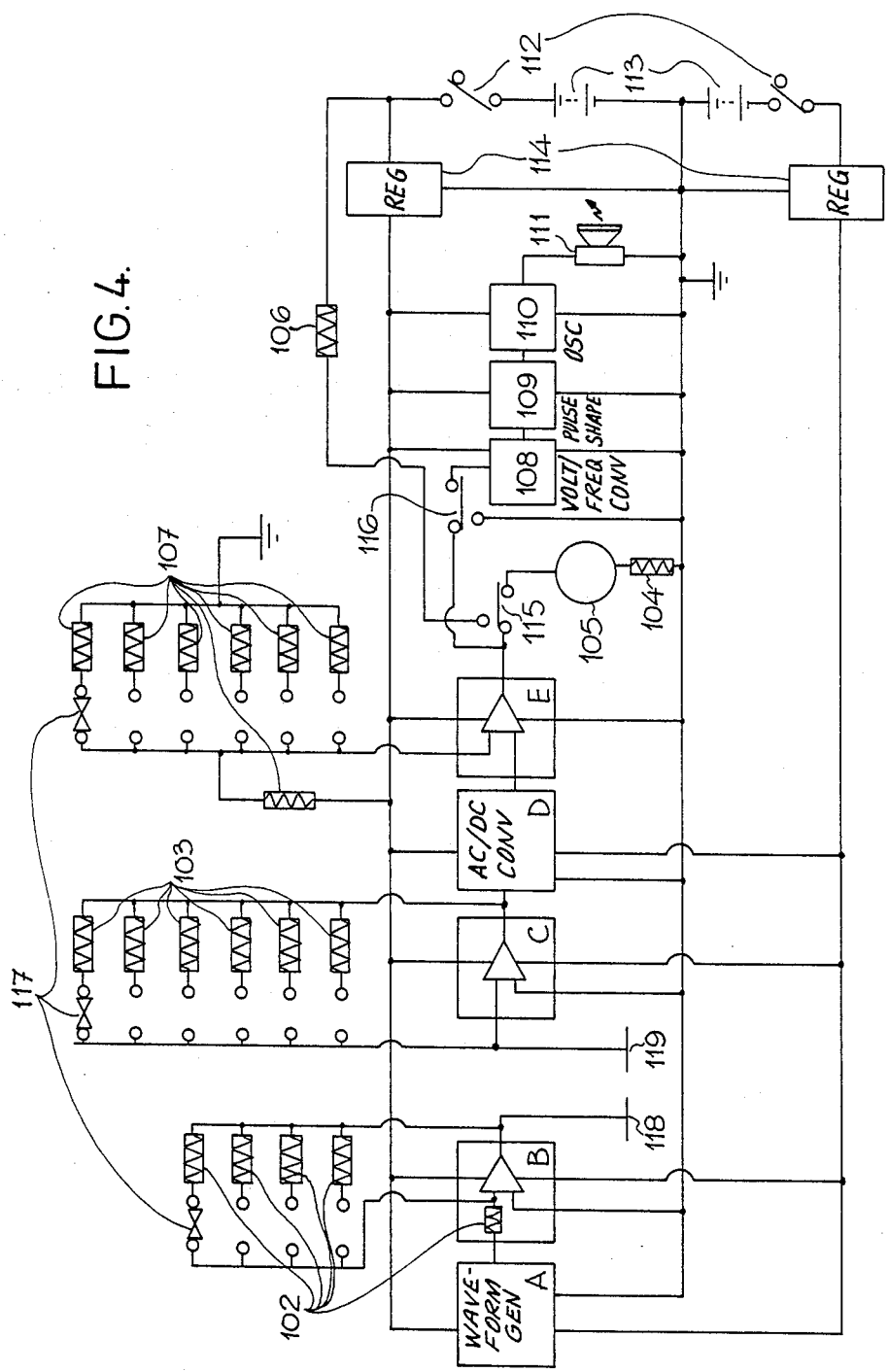
FIG. 4 is a schematic view of an electronic monitoring apparatus for use in the apparatus of FIGS. 1 or 3.

Referring now to the drawings, there is shown an apparatus 1 for use in performing the method of the invention which apparatus comprises a two-part casing 2, 3 held together by screws 4. The casing 2 has a handle 5; a range selecting switch 117; and openings for an analogue meter 105, on/off switch 112, an audible tone on/off switch 116, battery check switch 115, and an audio grill 12. Mounted inside the apparatus 1 is an electrode monitoring apparatus the schematic view of which is shown in FIG. 4. With respect to FIG. 2 of the drawings, there is mounted in co-planar relationship on the base of the casing 3 a pair of flat lamellar electrodes 118, 119. With respect to FIG. 3 of the drawings, there is mounted on the casing 3 by means of metal screws (not shown) in co-planar relationship a pair of curved lamellar electrodes 118a, 119a. The electrodes 118, 119 and 118a, 119a are composed of a polymeric composite such as carbon black impregnated elastomer mounted on a metal base 130, are each about 60 cm$^2$, and are separated by a gap of about 7 cm. The electrodes 118, 119 and 118a, 119a are connected by means of the screws to an electrode monitoring apparatus 101 shown in FIG. 4 which apparatus 101 may be used in both embodiments of the invention.

Referring to FIG. 4, the electrode monitoring apparatus 101 comprises a waveform generator A; amplifiers B, C and E; and an AC to DC converter D. The apparatus 101 further comprises gain control resistors 102, 103; a meter control resistor 104; the meter 105; a battery check resistor 106; zero offset resistors 107; a voltage-to-frequency converter 108 for generating an audible tone; a pulse shaping circuit 109; an audio oscillator 110; and an audible warning device 111. In addition, the apparatus 101 comprises the on/off switch 112, batteries 113, voltage regulators 114, the battery check switch 115; the audible tone on/off switch 116; and the range selecting switch 117.

In use, the waveform generator A feeds the amplifier B with a waveform. The waveform from the amplifier B is fed to the electrode 118. The waveform is detected by the electrode 119 and fed to the amplifier C which acts as a current to voltage converter. The output of the amplifier C is fed to the AC to DC converter D the output of which is fed to the amplifier E. The meter 105 and the voltage-to-frequency converter 108 are both fed by the output of the amplifier E.

The amplitude of the AC waveform which is fed to the AC to DC converter D is given by the value of the AC current through the polymeric composite between the electrodes 118, 119 or 118a, 119a, as appropriate, multiplied by the resistance of the resistor 103. The current through the polymeric composite is given by the amplitude of the waveform at the electrode 118 and 118a multiplied by the conductance of the polymeric composite. Thus, the DC voltage which is measured across the output of the amplifier E is in direct relationship with the value of the AC conductance of the polymeric composite between electrodes 118, 119 or 118a, 119a as appropriate. It will be appreciated that the essential difference between the electrodes 118, 119 and 118a, 119a is that the latter pair of electrodes are curved so as to fit snugly onto the profile of the side wall of a particular example of a polymeric composite viz a tire such as tire 20 shown in FIG. 5, in which apparatus 1 is placed on sidewall 21 of the tire. It will further be appreciated that the electrodes may have any appropriate shape depending on the configuration or shape of the polymeric composite under test. The electrodes should have a sufficiently large surface area so as to provide a coupling into the polymeric composite. The coupling serves to shunt the contact resistance of the polymeric composite. For a hand held instrument of the type shown as apparatus 1, an electrode area of 60 cm$^2$ is desirable.

EXAMPLE 1

A polymeric composite for test purposes was prepared by mixing 100 parts of styrene-butadiene rubber type 1502 with 50 parts carbon black type N-375, 3 parts zinc oxide, 1 part stearic acid, 1 part MBS (an accelerator for vulcanisation), and 1.75 parts sulphur, (all parts are by weight). The ingredients were incorporated into the rubber on an open mill which had a 4 mm nip and a friction ratio of 1.1:1.0. The total time required for incorporation of ingredients was about 30 minutes. After the ingredients were incorporated the compound was removed from the mill. The nip of the mill was closed to 2.2 mm and the compound returned for further mixing. Samples were removed after about 1, 4, 8 and 16 minutes and labelled B1, B4, B8 and B16, respectively. At the end of about 16 minutes the compound was removed from the mill. The compound was stored for 3 weeks and then returned to the mill for a further mixing for 19 minutes. A final sample was then taken and labelled B35.

A test piece, 210 mm in length and 90 mm in width, was cut from each sample B1, B4, B8, B16 and B35. The thickness of each test piece was measured at six different positions and the average thickness was calculated.

In order to measure the electrical conductance, one of the test pieces was placed on top of a 50 mm sheet of expanded polystyrene and the measuring apparatus 1 having the electrodes 118, 119 thereon was placed on top of the test piece so that the electrodes 118, 119 were in contact therewith. With the apparatus switched on, a sensitivity range was selected by rotation of the switch 117 so as to give a meter deflection of between 30% and 100% of full scale and the measurement of electrical conductance was read from the meter scale of the meter 105. Each of the other test pieces was measured in turn. Finally, the ambient temperature was measured and found to be about 17° C. The results are shown in Table 1 under "AC Conductance".

Comparison Method For comparison purposes, the DC electrical conductance of each test piece from Example A was measured.

In order to measure the DC electrical conductance of each of the test pieces, a pair of conventional electrodes was applied in turn to each test piece. The electrodes were of the tin foil and colloidal graphite type which are described in British Standard 2044:1978 Method 3. Each electrode was 5 mm wide and was applied transversely on both sides of the test piece. The distance between the electrodes was 70 mm and each electrode was approximately 70 mm from one end of the test piece. A DC voltage of 5 volts was applied to the pair of electrodes and the resulting current through the test piece was measured. The DC conductance of the test piece was calculated by dividing the measured current by the applied voltage. In addition the DC conductivity of the material was calculated as DC conductance times distance between electrodes over cross-sectional area.

The results of the measurements are described in Table 1. The data in Table 1 shows that a decrease in DC conductivity is associated with a decrease in AC conductance. It is well known that, except for extremely low states of distribution of carbon black, the DC conductivity decreases with increasing degree of dispersion of the carbon black. Hence, a measurement of AC conductance by the method of this invention provides an assessment of the degree of dispersion of carbon black.

TABLE 1

| SAMPLE | B1 | B4 | B8 | B16 | B35 |
| --- | --- | --- | --- | --- | --- |
| AVERAGE THICKNESS (mm) | 2.5 | 2.4 | 2.3 | 2.3 | 2.1 |
| AC CONDUCTANCE at 10,000 cycles/second (microsiemens) | 7.4 | 4.2 | 2.7 | 1.2 | 0.08 |
| DC CONDUCTANCE (microsiemens) | 12.6 | 5.2 | 3.0 | 0.94 | 0.004 |
| DC CONDUCTIVITY (millisiemens/meter) | 3.9 | 1.7 | 1.0 | 0.32 | 0.0015 |

EXAMPLE 2

The object of this example is to test whether or not the state of carbon black is uniform throughout a product. Non-uniformity might indicate a weakness in the product.

Figure 5:
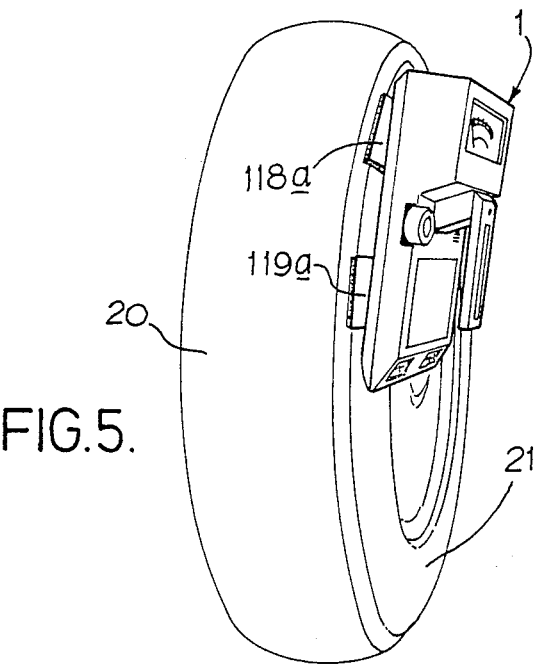
FIG. 5 is a perspective view of the apparatus of FIG. 3 in use on a tire.
Figure 6:
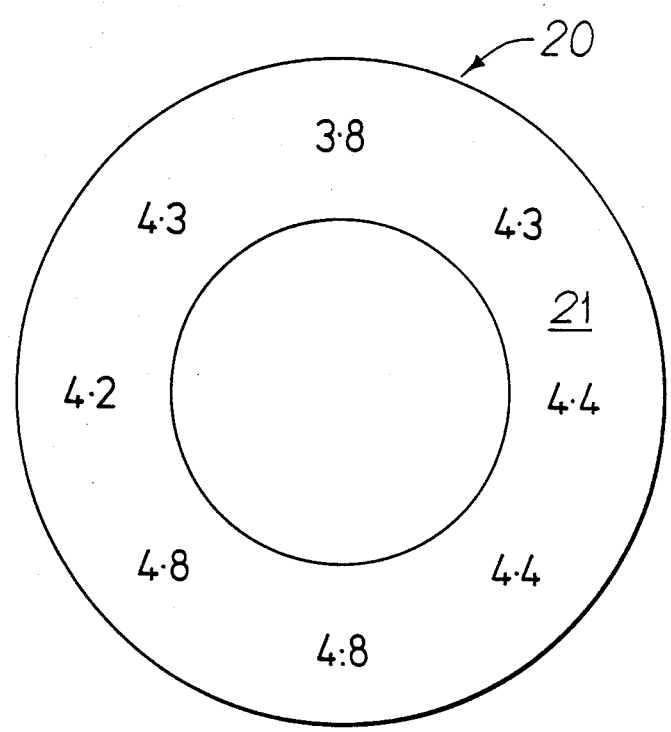
FIG. 6 is an elevation of the tyre of FIG. 5 showing results obtained with reference to Example 2 which follows.

The product in this example was a conventional tire 20 and as best seen in FIG. 5 of the drawings, the tire 20 was held in an upright position and the apparatus 1 having the electrodes 118a, 119a was placed on the sidewall 21 of the tire 20 in eight different positions around the circumference thereof. It will be appreciated that the electrodes 118a, 119a may be rotated about their mounting screws so as to mirror the profile of the tire 20. The readings obtained are shown schematically on the tire wall 21 of FIG. 6. It may be concluded that, as no exceptionally high value of AC conductance relative to the average value was recorded, all parts of the sidewall contain similar states of carbon black.

EXAMPLE 3

A series of four polymeric composites were prepared by mixing 100 parts of Standard Malaysian Rubber grade 20 with 50 parts carbon black type N-110, 5 parts Dutrex 729, 5 parts zinc oxide, 3 parts stearic acid and 2 parts Santoflex 13, (all parts are by weight). The four composites were prepared in an internal mixer and the mixing time was different for each mix in order to provide a range of carbon black dispersions. After mixing, each mix was sheeted off on an open mill and the four composites were labelled NR1, NR2, NR3 and NR4.

Test pieces, 210 mm in length and 25 mm in width, were cut from each composite sample for AC electrical conductance measurements. The thickness of each test piece was measured at six positions and the average thickness was calculated.

In order to carry out a measurement of AC electrical conductance, each of the test pieces was placed in turn on top of a 50 mm thick sheet of expanded polystyrene and the measuring apparatus 1 having electrodes 118, 119 was placed longitudinally on top of each test piece so that electrodes 118, 119 were in contact therewith. With the apparatus switched on, a sensitivity range was selected by rotation of the switch 117 so as to give an on-scale meter deflection and the measurement of AC electrical conductance was read from the scale of the meter 105. The ambient temperature was measured and found to be 170 C.

The AC electrical conductivity of the polymeric composite was calculated as the measured AC electrical conductance times distance along the test piece between the electrodes divided by the cross-section area of the test piece.

The results of these measurements are described in Table 2 under the heading "AC Electrical Conductance".

Comparison Method

A sample of each composite was assessed for dispersion by the method of the Cabot Dispersion Classification. The results are shown in Table 2. According to this system, the letter indicates the size and the cipher the abundance of undispersed carbon black agglomerates. Thus, A1 is the best dispersion and H6 the worst. This system also allows the "% carbon black dispersion" to be obtained. The procedure for obtaining the Cabot dispersion value is known and will not be given here.

The data in Table 2 show the correlation between the Cabot Dispersion Classification the AC electrical conductivity and the AC conductance. For example, composite NR1 shows the poorest Cabot dispersion and the highest conductivity and composite NR4 shows the best Cabot dispersion and the lowest conductivity.

TABLE 2

| POLYMERIC COMPOSITE | NR1 | NR2 | NR3 | NR4 |
|---|---|---|---|---|
| Average thickness in mm | 4.5 | 4.1 | 4.0 | 2.3 |
| AC Electrical conductance at 30,000 cycles/second, in microsiemens | 280 | 210 | 130 | 14 |
| AC Electrical conductivity at 30,000 cycles/second, in millisiemens/meter | 174 | 143 | 91 | 17 |
| Cabot Dispersion Classification: | | | | |
| rating | D1-D3 | C1-C3 | B1-B3 | A1-A2 |
| % carbon black dispersed | 96.5% | 98.2% | 99.2% | 99.8% |

Although in Examples 1-3, the apparatus 1 was used to take discrete measurements, it will be appreciated that continuous measurements may conveniently be taken using the same or a modified apparatus. Thus, the apparatus may be held stationary and the test piece may be on a continuous moving belt.

I claim:

1. A method for measuring the homogeneity of dispersion of a filler in a polymeric composite which method comprises applying two spaced apart capacitor plate electrodes closely adjacent the surface of the polymeric composite, a contact resistance inherently being provided between the capacitor plate electrodes and the polymeric composite, the polymeric composite exhibiting a conductance that is a function of the dispersion of said filler therein, the capacitor plate electrodes having a sufficiently large surface area for providing a capacitive coupling into the polymeric composite; applying an AC voltage between the electrodes of a frequency that effectively shunts said contact resistance; measuring the AC conductance through the polymeric composite from one electrode to the other electrode; and displaying the measured AC conductance so as to indicate the dispersion of filler in the composite.

2. A method as claimed in claim 1 wherein the electrodes are substantially co-planar.

3. A method as claimed in claim 1 which further comprises providing a waveform generator; feeding a waveform from the waveform generator to a first amplifier so as to amplify the waveform; feeding the amplified waveform to said one electrode; allowing the waveform to pass through the polymeric composite; detecting the waveform in the polymeric composite by means of said other electrode; feeding the detected waveform to a current to voltage converter; feeding the resultant AC voltage to an AC to DC converter so as to produce an output; feeding the output to a second amplifier so as to amplify the output; and providing means for displaying the output.

4. A method as claimed in claim 1 which further comprises moving the polymeric composite relative to the electrodes, which electrodes are closely adjacent the polymeric composite.

5. A method as claimed in claim 1 wherein the filler is carbon black.

6. A method as claimed in claim 1 wherein the polymeric composite is vulcanized.

7. A method as claimed in claim 1 wherein the polymeric composite is non-vulcanized.

8. A method as claimed in claim 1 wherein the electrode are on the surface of the polymeric composite.

* * * * *